(12) United States Patent
Bagger et al.

(10) Patent No.: US 8,809,522 B2
(45) Date of Patent: Aug. 19, 2014

(54) METHOD OF PREPARING A GLYCOSIDE OF A MONO- OR DIACYLGLYCEROL PRODUCT FROM A PLANT MATERIAL

(75) Inventors: Christian Lorentz Bagger, Karlslunde (DK); Arsalan Kharazmi, Hellerup (DK); Poul Hunniche Madsen, Rodby (DK); Thomas Nisgaard Brink, Nykobing F (DK)

(73) Assignee: Hyben Vital Licens ApS, Tranekaer (DK)

( * ) Notice: Subject to any disclaimer, the term of this patent is extended or adjusted under 35 U.S.C. 154(b) by 0 days.

(21) Appl. No.: 13/434,322

(22) Filed: Mar. 29, 2012

(65) Prior Publication Data

US 2012/0184023 A1    Jul. 19, 2012

Related U.S. Application Data

(63) Continuation of application No. 12/305,533, filed as application No. PCT/DK2006/000391 on Jul. 3, 2006.

(51) Int. Cl.
| | | |
|---|---|---|
| *C07H 1/06* | (2006.01) | |
| *C07H 1/08* | (2006.01) | |
| *C07H 15/10* | (2006.01) | |

(52) U.S. Cl.
CPC . *C07H 1/08* (2013.01); *C07H 15/10* (2013.01)
USPC ........................................... 536/128

(58) Field of Classification Search
None
See application file for complete search history.

(56) References Cited

U.S. PATENT DOCUMENTS

2002/0016299 A1* 2/2002 Sakai et al. ............... 514/23

FOREIGN PATENT DOCUMENTS

| JP | 2005-145949 A | 6/2005 |
| JP | 2005-343814 A | 12/2005 |
| WO | WO 03043613 A2 * | 5/2003 |

OTHER PUBLICATIONS

Salminen et al. Journal of Chromatography 1077 (2005) 170-180, Jun. 10, 2005.*
Jayaprakasam et al. J. Agric. Food Chem. 2004, 52, 6939-6943.*
Hanmoungjai et al. Journal of Chemical Technology and Biotechnology 77:771-776, 2002.*
Landbo et al. J. Agric. Food Chem. 2001, 49, 3169-3177.*
Amir Reza Jassbi, "Secondary Metabolites As Stimulants And Antifeedants Of *Salix integra* For The Leaf Beetle *Plagiodera versicolora*", Z. Naturforsch, 58C, 573-579 (2003).

(Continued)

*Primary Examiner* — Layla Bland
(74) *Attorney, Agent, or Firm* — William J. Sapone; Ware Fressola Maguire & Barber LLP (57) ABSTRACT

The present invention provides a method of preparing a glycoside of a mono- or diacylglycerol product from a plant material. The method comprises the steps of: (i) optionally milling the plant material, (ii) extracting the optionally milled plant material with a first aqueous extraction solution obtaining a first liquid phase and a first solid phase, (iii) separating the liquid phase from the solid phase to obtain a glycoside of mono- or diacylglycerol product, (iv) extracting the solid phase from step (iii) with a second extraction solution obtaining a second liquid phase and a second phase, and (v) separating the second liquid phase from the second solid phase to obtain a second and a third glycoside of mono- or diacylglycerol product, wherein the second extraction solution further comprises a cell wall degrading enzyme or a mixture of cell wall degrading enzymes.

29 Claims, 3 Drawing Sheets

(56) References Cited

OTHER PUBLICATIONS

Kharazmi, A. et al., "Rose hip inhibits chemotaxis and chemiluminescence of human peripheral blood neutrophils in vitro and reduces certain inflammatory parameters in vivo", Inflammopharmacology, Kluwer Academic Publishers, Dordrecht, NL, vol. 7, No. 4, 1999, pp. 377-386.

Winther, K. et al, "The Anti-Inflammatory Properties of Rose-Hip", Inflammopharmacology, vol. 7, No. 1, 1999, pp. 63-68.

Information Disclosure Statement Filed in Parent U.S. Appl. No. 12/305,533, filed Feb. 2, 2009, submitted Nov. 28, 2011 (References Omitted).

* cited by examiner

METHOD OF PREPARING A GLYCOSIDE OF A MONO- OR DIACYLGLYCEROL PRODUCT FROM A PLANT MATERIAL

CROSS REFERENCE TO RELATED APPLICATIONS

This application is a continuation of application Ser. No. 12/305,533, filed 18 Dec. 2008, which was a National Stage of PCT International Application no. PCT/DK2006/000391, filed 3 Jul. 2006.

FIELD OF THE INVENTION

The present invention relates to a method of preparing a glycoside of a mono- or diacylglycerol product from a plant material and to products obtained there from. In particular the present invention relates to the preparation of products comprising 3-β-D-galactopyranosyloxy-2-(octadeca-9Z,12Z,15Z-trienoyloxy)propanyl octadeca-9Z,12Z,15Z-trienoate, in particular from a rose hip materials.

BACKGROUND OF THE INVENTION

In U.S. Pat. No. 6,024,960, a rose-hip concentrate having a high content of vitamin C was found to alleviate the symptoms associated with inflammation. Specifically, the concentrate was obtained in accordance with a process of drying the milled rose hip under conditions which preserved a relatively high vitamin C content as well as the content of a number of other vitamins.

In the related U.S. Pat. No. 6,485,752 the oral administration of a combination of a rose-hip concentrate and fish oil is described as being useful in the alleviation of joint pain and stiffness, particularly in relation to arthritis. The method used for producing the rose-hip concentrate is the as the one described in U.S. Pat. No. 6,024,960 above.

Furthermore, WO 03/043613 relates to the use of glycosides of a mono- or diacylglycerol for treatment of inflammatory diseases, and more particularly to 3-β-D-galactopyranosyloxy-2-(octadeca-9Z,12Z,15Z-trienoyloxy)propanyloctadeca-9Z,12Z,15Z-trienoate (also known as GOPO) either obtained from natural sources such as rose hips (the fruits of *Rosa canina*) or prepared by total synthesis, for the treatment of inflammation. The action of this compound was shown to be alleviating chemiluminescence of polymorphonuclear monocytes and chemotaxis of mononuclear leukocytes. Moreover, it was discovered in WO 03/043613 that this compound could be obtained via an extraction, in particular an extraction using organic solvents, and a bio-guided fractionation procedure of rose-hips which was shown to contain this highly active anti-inflammatory agent. Similar to administering rose-hips orally was shown to efficiently alleviate inflammatory pains an oral formulation of the isolated anti-inflammatory agent was shown to be useful for treatment of symptoms associated with inflammation diseases.

Based on the knowledge that the activity of the glycoside of mono- or diacylglycerol compounds acts as an active ingredient capable of alleviating and treat inflammatory conditions in a mammal, it is of interest to develop improved methods for extracting and liberate said glycoside of a mono- or diacylglycerol compounds as well as developing new products comprising this active ingredient which are commercially interesting, provide a higher content of available active ingredient as well as a more safe and stable product using a more safe method.

SUMMARY OF THE INVENTION

Accordingly, in an aspect of the present invention a method of preparing a glycoside of a mono- or diacylglycerol product from a plant material may be provided. The method comprises the steps of: (i) optionally milling the plant material, (ii) extracting the optionally milled plant material with a first aqueous extraction solution obtaining a first liquid phase and a first solid phase, and (iii) separating the liquid phase from the solid phase to obtain a glycoside of mono- or diacylglycerol product.

In a further aspect of the present invention a juice product comprising the glycoside of mono- or diacylglycerol product which is obtainable by the method according to the present invention is provided.

In yet an aspect of the present invention a tincture product comprising the glycoside of mono- or diacylglycerol product obtainable by the method according to the present invention is provided.

In a further aspect of the present invention a solid concentrate comprising the glycoside of mono- or diacylglycerol product obtainable by the method according to the present invention is provided.

In an additional aspect of the present invention a product comprising the juice product, the tincture product and/or the solid concentrate may be provided.

The juice product, the tincture product, the solid concentrate or the product comprising the juice product, the tincture product or the solid concentrate is in an aspect provided for treating, alleviating, or preventing inflammatory conditions in a mammal in need therefore,

DETAILED DESCRIPTION OF THE INVENTION

The inventors of the present invention have surprisingly found that a plant material, such as rose hip, may be used as a source of producing several different extraction products comprising a mono- or diacylglycerol compound(s) which may act as a highly active anti-inflammatory agent.

Examples of such extraction products obtained from the plant material, such as rose hip, are juice products and solid concentrates as well as a tincture prepared by use of the invented methods may have a high content of galactolipids, such as the mono- or diacylglycerol compound(s). In addition the in vitro tests show that these preparations demonstrate potent anti-inflammatory as well as anti-oxidant activities. These in vitro findings correlate well with previous reports of the beneficial anti-inflammatory and anti-oxidant activity in treating inflammatory conditions in a mammal, such as joint stiffness in patients with osteoarthritis.

In a preferred embodiment of the present invention a method of preparing a glycoside of a mono- or diacylglycerol product from a plant material may be provided. The method comprises the steps of:

(i) optionally milling the plant material, (ii) extracting the optionally milled plant material with a first aqueous extraction solution obtaining a first liquid phase and a first solid phase, (iii) separating the liquid phase from the solid phase to obtain a glycoside of mono- or diacylglycerol product.

In step (i) the plant material may be milled before subjecting the plant material to the first extraction procedure in step (ii). In the present context the term "milled" relates to subjecting the plant material to chopping, crushed in a grinding mill or a combination of said handling steps. The plant material may also be treated by passing it through a separation step to remove nuts, hairs, and other extraneous matter that may have accompanied the plant material during harvesting. In an embodiment of the present invention the plant material may be dried before being milled.

The first extraction procedure in step (ii) may be performed at a first extraction temperature in the range of 20-110° C., such as in the range of 40-100° C., e.g. in the range of 60-95° C., such as in the range of 75-90° C., e.g. 90° C. Preferably, the first extraction procedure in step (ii) may be performed in a period ranging from 10 seconds to 20 minutes, such as ranging from 30 seconds to 10 minutes, e.g. ranging from 45 seconds to 5 minutes, such as ranging from 1 minute to 2 minutes, e.g. approximately 1 minute.

The above method may further comprise the step of:

(iv) extracting the solid phase obtained from step (iii) with a second extraction solution obtaining a second liquid phase and a second solid phase.

The second extraction procedure in step (iv) may be performed at a second extraction temperature in the range of 20-75° C., such as in the range of 30-60° C., e.g. in the range of 40-55° C., such as in the range of 45-50° C., e.g. 50° C. Preferably, the second extraction procedure in step (iv) may be continued for a period of time in the range of 1 minute to 500 minutes, such as from 10 minutes to 400 minutes, e.g. from 50 minutes to 300 minutes, such as from 100 minutes to 200 minutes, e.g. from 120 minutes to 180 minutes, such as 180 minutes.

In an embodiment of the preset invention the pH of the second extraction procedure in step (iv) may be adjusted to a pH value in the range of pH 1-10, such as in the range of pH 2-9, e.g. in the range of pH 3-7, such as in the range of pH 4-6, e.g. pH 4.5. In an embodiment of the present invention the pH may be adjusted with NaOH or HCl, In a preferred embodiment of the present invention the second extraction solution further comprises a cell wall degrading enzyme or a mixture of cell wall degrading enzymes. In the present context the term "cell wall degrading enzyme" relates to enzymes capable of degrading the cell wall to release intracellular components from the plant material. A number of different cell wall degrading enzymes and enzyme mixtures are commercially available, such as Ceiluclast 1.5 L, Finizym 200 L, Ultraflo L and Viscozyme L from Novozymes A/S. The enzyme mixtures may comprise different enzymatic activities such as cellulase, β-glucanase, xylanase, arabanase, pentosanase.

The cell wail degrading enzyme may be one or more enzymes selected from the group consisting of cellulase, β-glucanase, xylanase, arabanase and pentosanase, such as 2 or more of said enzymes, e.g. 3 or more of said enzymes, such as 4 of said enzymes. When two or more cell wall degrading enzymes are added to the second extraction process in step (iv), it is a mixture of cell wall degrading enzymes.

In an embodiment of the present invention the described pH adjustment may be adjusted in such a way as to provide a pH value deviating at most 4 pH units from the optimum of a cell wail degrading enzyme or from the optimum activity of a mixture of cell wall degrading enzymes.

When the second extraction process in step (iv) is completed the enzymatic activity may be inactivated, preferably before obtaining one or more glycoside of mono- or diacylglycerol product(s). This inactivation may be achieved by heat or by addition of an acid or a base in a preferred embodiment of the present invention the inactivation of the enzymatic activity is achieved by increasing the temperature of the second extraction medium, preferably to a temperature of at least 30° C., such as at least 40° C., e.g. at least 50° C., such as at least 60° C., e.g. at least 70° C. such as at least 80° C., e.g. at least 90° C. such as at least 100° C., e.g. at least 110° C.

The above method may further comprise the step of:

(v) separating the second liquid phase from the second solid phase to obtain a second and a third glycoside of mono- or diacylglycerol product.

To separate the first and/or second solid phase from the first and/or second liquid phase as described above in step (iii) and/or in step (v) the separation may be performed by decanting, centrifugation, filtration or a combination hereof.

In a preferred embodiment of the present invention the first and/or second aqueous extraction solution is water. Preferably, the above described extraction step (ii) and/or extraction step (iv) does not involve the use of organic solvents.

In a preferred embodiment of the present invention the first, second and third glycoside of mono- or diacylglycerol products may be produced in one combined process of all steps (i) to step (v).

In the present context the term "plant material" relates to a material that may be obtained from the group consisting of rose hip, preferably, the rose hip is obtained from wild rose bushes, in particular the rose hip is selected from the group consisting of *Rosa canina* ("dog rose-hip"), *Rosa gallica, Rosa condita, Rosa rugosa, Rosa hugonis, Rosa nitida, Rosa pendulina, Rosa pimpinellifolia*, and *Rosa sericea*; fruit, vegetable and cereal, preferably, the fruit, vegetable and cereal is selected from the group consisting of olive (e.g. *Olea europaea*), alfalfa (e.g. *Mediargo sativa* L.), soya bean (e.g. *Glycine max*), potato (e.g. *Salanum Turerosum* L.), pepper (e.g. *Capsicum annuum* L), oat (e.g. *Avena sativa*), wall cress (e.g. *Arabidopsis thaliana*), *Petunia hybrida*, lyme grass (e.g. *Elymus arenarius*), broom (e.g. *Sarothamnus scoparius*), coltsfoot (e.g. *Tussilago farfara*), chenopodiaceae, seakale (e.g. *Crambe maritima*), sloe (e.g. *Prunus spinosa*), eryngo (e.g, *Eryngium*), sea purslane (e.g. *Honckenya peploides*), blackberry, mountain ash (e.g. *Sorbus aucuparia*), service tree (e.g, *Sorbus domestica*), sea buckthorn (e.g. *Hippophaë rhamnoides*), hemp agrimony (e.g. *Eupatorium cannabinum*), cucumber (e.g. *M. charantia* or *M. rustrata*), *Catharanthus roseus*, yew (e.g, *Taxus baccata*), mistletoe (e.g. *Viscum album*), padderok (e.g. *M. arvense*), meadowsweet (e.g. *Filipendula ulmaria*), dropwort (e.g. *F. hexapetala*), Ephidera (e.g. *E. sp.*), reed (e.g. *Phragmites communis*), ground ivy (e.g. *Glechoma hederacea*), male fern (e.g. *Lastrea filix mas*), shield fern (e.g. *Dryopteris*) and lady's mantle (e.g. *Alchemilla vulgaris*); seaweed, preferably, the seaweed is selected from the group consisting of *Anfeltia tobuchiensis* (Rhodophyta), *Laminaria japonica, Sargassum pailidum* (Phaeophyta), *Ulva fenestrate* (Chlorophyta), *Zostera marina* (Embriophyta), sea wrack (*Fucus vesiculosus*), green alga (*Chlorelia vulgaris*), Cyanobacteria (e.g. *Phormidium tenue*) and Okinawan Marine Sponge (*Phyllospongia Foliascens*).

In an embodiment of the present invention the part of the plant, the vegetable and the cereal that may be useful is selected from the group consisting of the leaf, the stalk, the fruit, the root or any combination hereof.

In order to achieve a sufficient extraction of the plant material the first aqueous extraction solution and the plant material is mixed at a ratio in the range of 100:1 to 1:100, preferably at the ratio in the range of 50:1 to 1:50, such as in the range of 25:1 to 1:25, preferably at the ratio in the range of 10:1. Furthermore, the second aqueous extraction solution and the plant material may be mixed at a ratio in the range of 50:1 to 1:50, preferably at the ratio in the range of 25:1 to 1:25, such as in the range of 10:1 to 1:10, preferably at the ratio of 5:1.

The above method is suitable for preparing a glycoside of a mono- or diacylglycerol product from a plant material.

Preferably, the glycoside of a mono- or diacylglycerol product may be in the form a juice product, a tincture product and/or a solid concentrate.

In a preferred embodiment of the present invention the first liquid phase obtained in step (iii) comprises a first glycoside of mono- or diacylglycerol product. Preferably, the first glycoside of mono- or diacylglycerol product obtained from step (iii) may be comprised in a juice product.

In yet a preferred embodiment of the present invention the second liquid phase obtained from step (v) may comprise a second glycoside of mono- or diacylglycerol product. Preferably the second glycoside of mono- or diacylglycerol product may be comprised in a tincture product.

In a further preferred embodiment of the present invention the second solid phase obtained in step (v) may comprise a third glycoside of mono- or diacylglycerol product. Preferably, the third glycoside of mono- or diacylglycerol product may be comprised in a solid concentrate.

The solid concentrate according to the present invention may be dried. The dried concentrate may be in the form of a powder or granular material, preferably having a particle size of below 1 mm, with about 0.1 to 0.5 mm as the most preferred. In the present context the term "powder" will be used to cover the full spectrum of the dried solid concentration in whatever solid form it takes.

In a preferred embodiment of the present invention the product, the juice product, the tincture product and/or the solid concentrate is a glycoside of mono- or diacylglycerol enriched product.

The juice product, the tincture product and/or the solid concentrate may be incorporated within or used on many of the foods and beverages one can consume on a daily basis. Suitable foods and beverages which could be made, include but are not limited to, nutritional beverages, soft drinks, fruit beverages and juices, electrolyte containing beverages, puddings, baked goods (i.e., cookies, brownies, fudge, cake, breads), non-baked extruded foods (i.e., bars), salad dressings, condiments, confections (i.e., candy), snack foods (i.e., chips, pretzels, tortillas), drips and spreads, ice cream, chewing gum, candies, frozen confections and novelties, dairy products such as yogurt, margarine-like spreads, seasonings such as for meat, poultry, seafood and salads. Fat free, reduced fat and low calorie versions of these foods are embraced by the present invention.

Incorporation of the juice product, the tincture product and/or the solid concentrate of the present invention into foods/beverages may provide the advantages of patient compliance over a prolonged period of use and in a form which may be more desirable to the consumer, rather than in the form of e.g. a medicament.

Furthermore, the juice product, the tincture product and/or the solid concentrate may be incorporated or formulated within or used on a natural medicine product, a dietary supplement or a pharmaceutical product.

The term "glycosides of mono- or diacylglycerol" and similar terms are intended to mean a class of glycosides of mono- or diacylglycerol (as well as ethers), such as those which can be isolated from plants e.g. as illustrated by the present invention, and which are not esters of eicosapentaenoic acid. The "glycoside" part is typically a pentose, hexose or heptose, in particular hexoses such as galactose and glucose, e.g. galactose, but can also be di- and oligosaccharides containing two or more sugar moieties in combination, in particular diglycosides such as digalactosides and diglucosides, e.g. 6-O-(α-D-galactopyranosyl)-α-D-galactopyranose.

In the present context the term "glycosides of mono- or diacylglycerol product" relates to a product obtained from a plant material comprising a glycoside of mono- or diacylglycerol compound. The glycosides of mono- or diacylglycerol product may be obtained from the plant material by isolation by means of chromatography, microfiltration, filtration, centrifugation, extraction or any combination hereof.

In an embodiment of the present invention the glycosides of mono- or diacylglycerol compound may have the formula 1:

wherein R and R' independently are selected from hydrogen, $C_{10-24}$-alkyl, and $C_{10-24}$-acyl, said alkyl and acyl groups having 0 to 5 unsaturated bonds, and $R^1$, $R^2$, $R^3$ and $R^4$ independently are selected from hydrogen and glycoside moieties; with the first proviso that not both of R and R' are hydrogen, and with the second proviso that none of R and R' is eicosapentaenoyl.

The "wavy bonds" in the formulae presented herein are intended to mean that the carbon on which the substituent in question is positioned may be in the (R) or (S) configuration. In the "sugar" moiety (glycoside) the two different configurations are some times designated α and β. A particular interesting combination is glucose or galactose in the β-pyranose form.

Although the "sugar" moiety in the formulae presented herein is drawn in the pyranose form, it will be understood that the anti-inflammatory agent may also be present in the furanose form (or a mixture of the pyranose and furanose forms) as a solid and in solution.

In the present context, the term "$C_{10-24}$-alkyl" is intended to mean a linear or branched hydrocarbon group having 10 to 24 carbon atoms, e.g., decyl, undecyl, dodecyl, tetradecyl, hexadecyl, octadecyl, nonadecyl, eicodecyl, etc.

In the present context, the term "$C_{10-24}$-acyl" is intended to mean a linear or branched hydrocarbon group having 10 to 24 carbon atoms wherein the first carbon of the group is a carbonyl ($C_{9-23}$-alkyl-C(=O)—), i.e. a fatty acid residue having 10 to 24 carbon atoms. Examples hereof are the residues of lauric acid (C12), myristic acid (C14), palmitic acid (C16), stearic acid (C18), etc.

The alkyl and acyl groups may have 0 to 5 unsaturated bonds such as double or triple bonds, in particular double bonds. Examples of acyl groups having one or more unsaturated double bonds are the residues of palitoleic acid (C16:1), oleic acid (C18:1), linoleic acid (C18:2), linolenic acid (C18:3), arachidonic acid (C20:3), retinoic acid (C20:5), etc.

More specifically, the glycosides of mono- or diesters (or ethers) of glycerol are diesters, diethers, or monoether-monoesters, i.e. R and R' are independently selected from $C_{10-24}$-alkyl and $C_{10-24}$-acyl.

The currently most preferred are glycosides of diesters, i.e. R and $R^I$ are independently $C_{10-24}$-acyl. In all instances, the alkyl and acyl groups have 0 to 5 unsaturated bonds.

With respect to the degree of saturation of the alkyl and acyl groups, it is currently believed that any alkyl and acyl groups having 0 to 4 unsaturated bonds, such as 1-3 unsaturated bonds, e.g. 2 or 3 unsaturated bonds, in particular 3 unsaturated bonds, are the most suitable as R and R'.

Also, it is currently believed that any unsaturated bonds preferably are double bonds.

This being said, it is envisaged that particularly interesting anti-inflammatory agents are those where R and R' both are $C_{16-20}$-acyl having 1 to 3 double bonds, such as $C_{18}$-acyl having 3 double bonds, in particular where the "sugar" moiety is glucose or galactose, in particular galactose.

As mentioned above, $R^1$, $R^2$, $R^3$ and $R^4$ are independently selected from hydrogen and glycoside moieties, preferably only at the most one of $R^1$, $R^2$, $R^3$ and $R^4$ is a glycoside moiety. The latter embodiment relates to compounds that are often found in vegetable sources along with compounds where all of $R^1$, $R^2$, $R^3$ and $R^4$ are hydrogen. In some interesting embodiments, all of $R^1$, $R^2$, R3 and $R^4$ are selected hydrogen.

The term "glycoside moieties" is intended to mean a mono- or disaccharide moiety, e.g. derived from O-galactopyranose, O-glucopyranose, O-galactopyranosylgalactopyranose, O-glucopyranosylgalactopyranose, O-galaotopyranosyiglucopyranose and O-glucopyranosyiglucopyranose.

Also, it is envisaged that the glycoside of a mono- or diacylglycerol compound preferably has the formula II:

wherein R, $R^1$, $R^2$, $R^3$ and $R^4$ all are as defined above.

More specific examples of the glycoside of a mono- or diacylglycerol compound of particular interest are those selected from β-D-galactopyranosyl derivatives, α-D-galactopyranosyl derivatives, β-D-glucopyranosyl derivatives, and α-D glucopyranosyl derivatives, such as β-D-galactopyranosyl and 6-O-(α-D-galactopyranosyl)-β-D-galactopyranosyl derivatives.

Even more specific examples of the glycoside of a mono- or diacylglycerol compound are 3 β-D-galactopyranosyloxy-2-(octadeca-9Z,12Z,15Z-trienoyloxy)propanyl octadeca-9Z, 12Z,15Z-trienoate, 3-β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,l2Z, l5Z trienoyloxy) propanyl octadeca-9Z,12Z,15Z-trienoate, 3-α-D-glucopyranosyloxy-2-(octadeca-9Z,12Z,15Z-trienoyloxy)propanyl octadeca-9Z,12Z,15Z-trienoate, 6-O-(α-D-galactopyranosyl)-3 β-D-galactopyranosyloxy-2-(octadeca-9Z, 12Z,15Z-trienoyloxy)propanyl octadeca-9Z,12Z,l5Z-trienoate and 6-O-(α-D-galactopyranosyl)-3-α-D-galactopyranosyloxy-2-(octadeca-9Z,12Z,15Z-trienoyloxy) propanyl octadeca-9Z,12Z,15Z-trienoate, such as 3-β-D-galactopyranosyloxy-2-(octadeca-9Z,l2Z,l5Z-trienoyloxy) propanyl octadeca-9Z,12Z,15Z-trienoate or 3-β-D-glucopyranosyloxy-2-(octadeca-9Z,12Z,15Z trienoyloxy) propanyl octadeca-9Z,12Z,15Z-trienoate, e.g. 3-β-D-galactopyranosyloxy-2-(octadeca-9Z,12Z,15Z-trienoyloxy) propanyloctadeca-9Z,l 2Z,15Z-trienoate which can be isolated from rose-hips.

Figure 1:
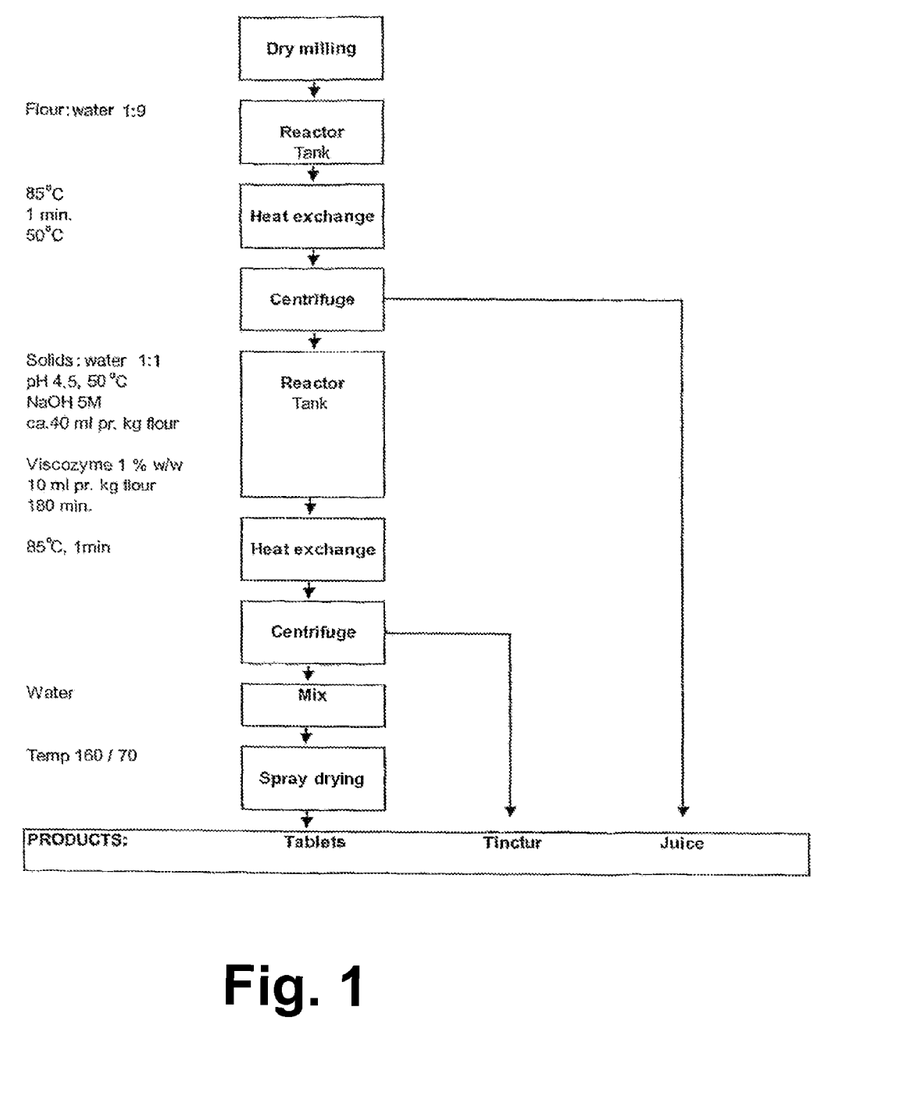
FIG. 1 shows a process layout of the present invention.

In an embodiment of the present invention (as may be illustrated by the process layout in FIG. 1) the plant material is optionally dry milled followed by mixing the milled plant material in a reactor tank with a first aqueous extraction solution, such as water, at a ratio of plant material to first aqueous extraction solution as described in the specification, such as in a ratio of 1:9. The first extraction process is performed at a temperature as described in the specification, such as a temperature of 85° C. and continued for a period of time as defined in the specification, such as 1 minute, The first extraction process is ended by a separation step, preferably by centrifugation, to obtain a first liquid phase and a first solid phase, The resulting first solid phase is subsequently mixed with a second aqueous extraction solution in a reactor tank as described in the specification, such as in a ratio of 1:1 and the temperature of this second extraction process is as de-scribed in the specification, such as 50° C. and the pH is adjusted as described in the specification, such as to pH 4.5 with 5M NaOH. Furthermore, a cell wall degrading enzyme or a mixture of cell wall degrading enzymes, such as Viscozyme (1% w/w), is added to the second extraction process and the second extraction process is continued for a period of time as de-scribed in the specification, such as for 180 min. The enzymatic activity is subsequently terminated as described in the specification, such as by in-creasing the temperature to 85° C., for approximately 1 minute (sufficient to inactivate the enzymatic activity). This second extraction process is ended by a separation step, such as centrifugation, to obtain a second liquid phase and a second solid phase. The obtained first liquid phase, second liquid phase and the second solid phase results in a first glycoside of mono- or diacylglycerol product, a second glycoside of mono- or diacylglycerol product and a third glycoside of mono- or diacylglycerol product, respectively. These first, second and third glycoside of mono- or diacylglycerol products may be comprised in a juice product, a tincture product and a solid concentrate. Preferably the solid concentrate is dried, preferably using a spray dryer, to obtain a dry solid concentrate.

In an embodiment of the present invention the first glycoside of mono- or diacylglycerol product, the second glycoside of mono- or diacylglycerol product and the third glycoside of mono- or diacylglycerol product are structurally similar products, or substantially similar products, but differs from each other by being obtained from different extractions of the plant material.

In yet an embodiment of the present invention the first glycoside of mono- or diacylglycerol product, the second glycoside of mono- or diacylglycerol product and the third glycoside of mono- or diacylglycerol product may comprise a combination of varies compounds failing within the scope of the glycoside of mono- or diacylglycerol compound according to the present invention.

In an embodiment of the present invention the method of preparing a glycoside of a mono- or diacylglycerol product from a plant material comprises the steps of: (i) optionally milling the plant material, (ii) extracting the optionally milled plant material with a first aqueous extraction solution obtaining a first liquid phase and a first solid phase, (iii) separating the liquid phase from the solid phase to obtain a glycoside of mono- or diacylglycerol product, (iv) extracting the solid phase from step (iii) with a second ex-traction solution obtaining a second liquid phase and a second solid phase, and (v) separating the second liquid phase from the second solid phase to obtain a second and a third glycoside of mono- or diacylglycerol product, wherein the second extraction solution further comprises a cell wall de-grading enzyme or a mixture of cell wall degrading enzymes.

A medicament comprising the juice product, the tincture product or the solid concentrate may be used for the prevention, treatment or alleviation of inflammation, whether caused by illness or medical conditions, such as viral or bacterial diseases (commonly termed "inflammatory conditions"). Inflammation" is defined in Stedman's Medical Dictionary, 26$^{th}$ Edition as "a fundamental pathologic process consisting of a dynamic mixture of cytological and chemical reactions that occur in the affected blood vessels and adjacent tissue in response to injury or abnormal stimulation caused by physical, chemical or biological agent, including the local reactions and resulting morphologic changes, the destruction of removal of the injurious material, and the responses that lead to repair and healing". Examples of relevant inflammatory conditions are hepatitis, meningitis, rheumatoid arthritis, inflammatory bowel diseases such as Crohn's disease, allergic syndromes, diabetes, congestive heart disease, psoriatic, reactive or osteoarthritis or other arthritides such as osteoarthrosis, multiple sclerosis, atherosclerosis, sepsis/septic shock, dermal inflammation, graft rejection, and inflammation secondary to chemotherapy or radiotherapy of neoplastic disease.

The present invention is presently believed to be particularly suitable for the treatment of arthritis and/or osteoarthrosis.

Administration may proceed by oral, buccal, parenteral, topical, rectal, transdermal or intranasal administration, though oral administration is preferred, The term "mammal" is intended to include larger mammals such as humans as well as domestic or farm animals such as horses, dogs, sheep, pigs, cows, etc. Among these mammals, humans are particularly interesting subjects to benefit form the invention.

As mentioned above the juice product, the tincture product or the solid concentrate can be formulated for delivery via various routes of administration. Oral administration is preferred for ease of use. A unit dosage can comprise a therapeutically effective amount of the juice product, tincture product or the solid concentrate for a single daily administration (e.g. orally or by feeding tube in an enteral diet for example), or be formulated to provide multiple doses per day. A unit dosage will depend on many factors including age, condition, and disease state, but in any event, the entire daily dosage will be that which is physiologically acceptable to the individual and can be administered daily over a prolonged period of time.

While still under investigation, it is believed that a dosage of from 0.001-50 mg/kg body weight per day, such as 0.005-20 mg/kg body weight per day (mg/kg/day) of the glycoside of mono- or diacylglycerol compounds in the juice product, tincture product or the solid concentrate, would be effective in the treatment of the inflammatory condition, in particular arthritis and osteoarthrosis, and relief of the symptoms associated therewith. A similar to lesser dose rate could be administered on a daily basis as a prophylactic.

In a further embodiment of the present invention the medicament may be in the form of a daily dose form applicable for administration of about 0.005-50 mg/kg body weight per day of the glycoside of mono- or diacylglycerol compounds in the juice product, tincture product or the solid concentrate, in unitary or multiple doses.

A preferred unit dose is from about 0.001 to about 50, such as 0.001-20, mg/kg/day. The total daily dose would be about 0.1 to about 5000 mg/day, such as 0.5-500 mg/day. For example, the unit dose may be administered by compounding into tablets or capsules, each containing from 0.01-500 mg of the glycoside of mono- or diacylglycerol compounds in the juice product, tincture product or the solid concentrate, such as 3-β-D-galactopyranosyloxy-2-(octadeea-9Z,12Z,15Z-trienoyloxy)propanyloetadeca-9Z,12Z,15Z-trienoate, the user taking from one to four capsules per day.

The invention will be further disclosed in the following non-limiting figures and the following non-limiting examples.

EXAMPLES

Example 1

The plant material is raw material hulls of Rose hip are milled.

Water and milled hulls of Rose hip is mixed (10:1) at 90° C. for 1 minute.

The mixture is separated by centrifugation, 10 minutes at 3000 rpm.

The aqueous phase obtained, showed to comprise the glycoside of mono- or diacylglycerol compound and is principally ready to be bottled as a juice product.

Water is added to the solid phase (5:1) and the temperature is adjusted to 50° C. and pH is adjusted to 4.5 with 2 M NaOH.

Viscozyme L (Novozymes A/S) is added as 2% v/w of initial raw material of rose hip and the enzyme reaction is carried out for 180 minutes.

After 180 minutes the mixture is heated to 85° C. for 1 minute to inactivate the enzyme activity.

After inactivation the mixture is separated by centrifugation 10 minutes at 3000 rpm.

The solid phase obtained, showed to comprise the glycoside of mono- or diacylglycerol compound and is ready to be applied as a solid concentrate and may principally be ready to be applied in tablets etc.

The aqueous phase obtained, showed to comprise the glycoside of mono- or diacylglycerol compound and is principally ready to be applied in tinctures.

Example 2

Biological Activities
Methods
The anti-inflammatory as well as anti-oxidant activities of different extracts (concentrates) were determined as a measure of their biological activity.

Chemotaxis. The anti-inflammatory activity of the extracts was measured by a chemotaxis assay. This assay measures the migration of human peripheral blood polymorphonuclear leukocytes (PMNs) towards a biologically active chemoatrractant. The assay is widely used as a measure of in vitro inflammation. Briefly, the cells are pre-incubated with various concentrations of the extract. Following preincubation the migration of the cells are determined.

Chemiluminescence. The anti-oxidant activity of the extracts was measured by a chemiluminescence assay. This assay measures the oxidtavive burst response of activated human peripheral blood polymorphonuclear leukocytes (PMNs). The activated cells generate reactive oxygen radicals. The cells are preincubated with various concentrations of the extract. Following preincubation the cells are activated by known activators such as opsonized zymosan particles, and then the generation of oxygen radicals by activated cells are determined.

In both assays the cells were obtained from peripheral blood of healthy subjects.

Results

Figure 2:
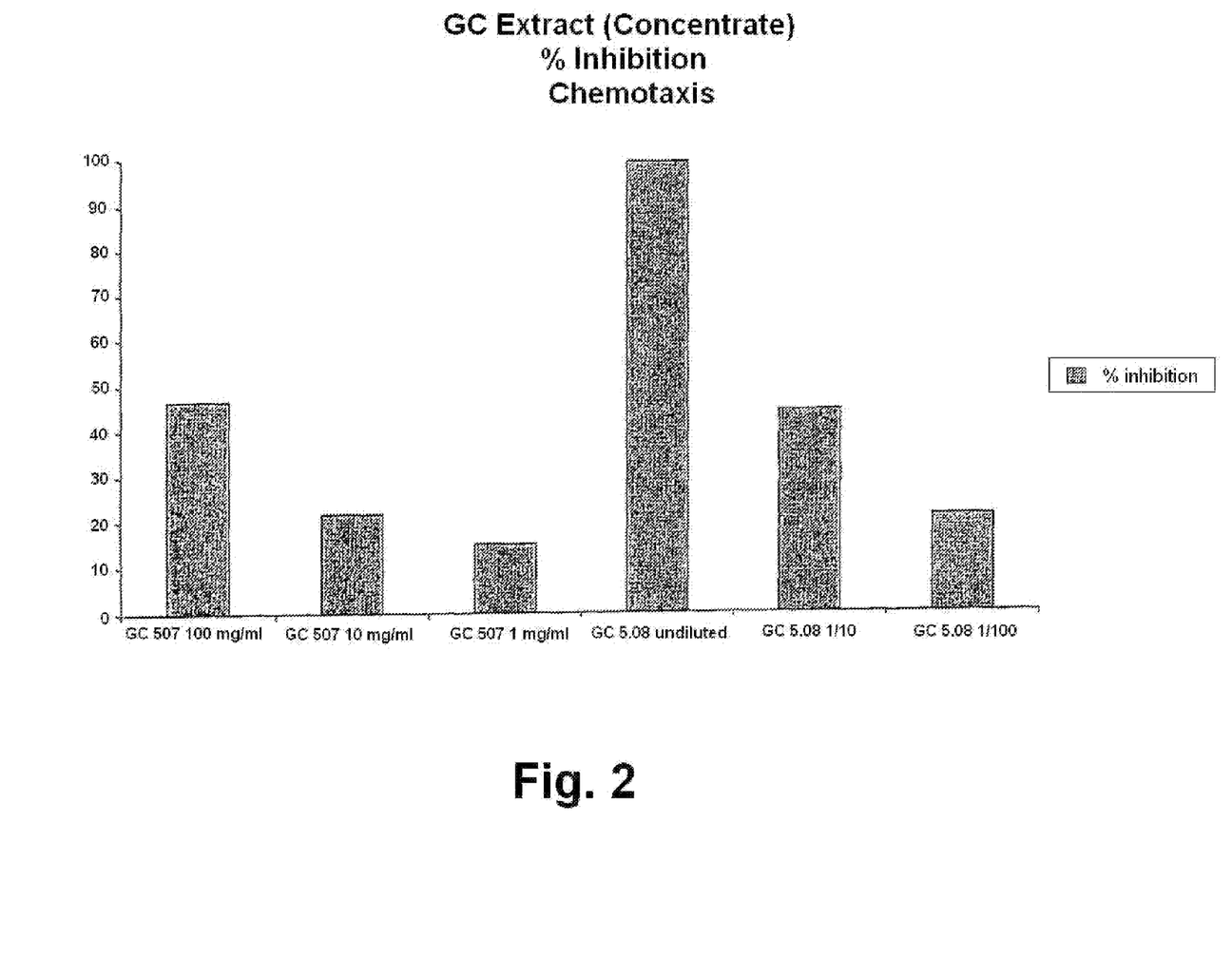
FIG. 2 shows the effect of rose hip concentrates on migration (theme-taxis) of human peripheral blood leukocytes as an anti-inflammatory activity. The results are mean of 3 experiments.
Figure 3:
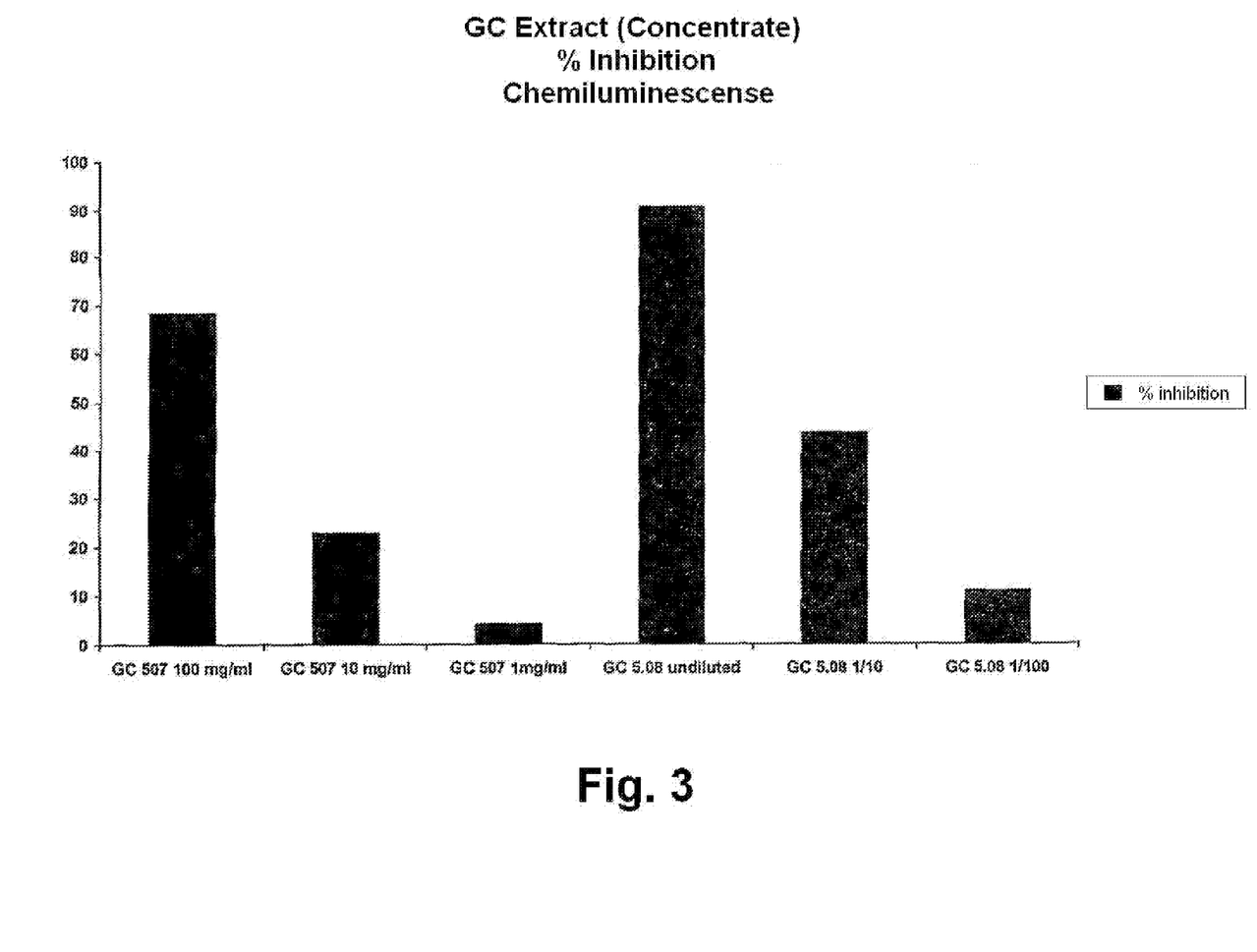
FIG. 3 shows the effect of rose hip concentrates on oxidative burst response (chemiluminescence) of human peripheral blood leukocytes. The results are mean of 3 experiments.

As shown in FIGS. 2 and 3 both the pellet (GC507) water extract (GC508) inhibited chemotaxis in a concentration-dependent manner at concentrations as low as 10 mg/ml, or a dilution of 1/10.

Similar findings were found regarding the inhibition of chemiluminescence response (FIG. 2) as a measure of anti-oxidant activity (FIG. 3)

CONCLUSIONS

These results presented in this invention show that both the extract as well as the pellet demonstrate considerable anti-inflammatory as well as anti-oxidant activities. Another advantage of this process is that the enzymes, which potentially might destroy the active ingredient GOPO are neutralized by this process thereby making GOPO stable. Another advantage of this process is that the eventual oxidation of the active ingredient GOPO is prevented by this process.

The invention claimed is:

1. A method of obtaining a product containing at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,12Z,15Z trienoyloxy)propanyl octadeca-9Z,12Z,15Z-trienoate, 3-α-D-glucopyranosyloxy-2-(octadeca-9Z,12Z,15Z-trienoyloxy) propanyl octadeca-9Z,12Z,15Z-trienoate, and mixtures thereof from a plant material, said method consisting of the following steps, taken in sequence, of:

obtaining a plant material which contains at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,12Z,15Z trienoyloxy)propanyl octadeca-9Z,12Z,15Z-trienoate, 3-α-D-glucopyranosyloxy-2-(octadeca-9Z,12Z,15Z-trienoyloxy)propanyl octadeca-9Z,12Z,15Z-trienoate, and mixtures thereof;

(i) optionally milling the plant material, (ii) extracting the optionally milled plant material with water and producing a first liquid phase and a first solid phase which contains the at least one glycoside of a mono- or diacylglycerol;

(iii) separating the first liquid phase from the first solid phase, wherein the separated first liquid phase comprises a liquid product containing a glycoside of mono- or diacylglycerol, (iv) extracting the first solid phase obtained from step (iii) with water and producing a second liquid phase and a second solid phase which contains the at least one glycoside of a mono- or diacylglycerol, and, (v) separating the second liquid phase from the second solid phase to obtain in the second solid phase a solid concentrate product containing a concentrate of the at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,12Z,15Z trienoyloxy)propanyl octadeca-9Z,12Z,15Z-trienoate, 3-α-D-glucopyranosyloxy-2-(octadeca-9Z,12Z,15Z-trienoyloxy)propanyl octadeca-9Z,12Z,15Z-trienoate, and mixtures thereof, and, wherein no organic solvents are used in any of steps i-v.

2. The method according to claim 1 further comprising mixing the water in step (ii) or the water in step (iv) with the plant material or the first solid phase at a ratio of 50:1 to 1:50.

3. The method according to claim 1 further comprising mixing the water in step (ii) or the water in step (iv) with the plant material or the first solid phase at a ratio of 25:1 to 1:25.

4. The method according to claim 1 further comprising mixing the water in step (ii) or the water in step (iv) with the plant material or the first solid phase at a ratio of 10:1 to 1:10.

5. The method according to claim 1 further comprising performing the extracting step (iv) at an extraction temperature in the range of 20-75° C.

6. The method according to claim 1 further comprising performing the extracting step (iv) at an extraction temperature in the range of 30-60° C.

7. The method according to claim 1 further comprising performing the extracting step (iv) at an extraction temperature in the range of 40-55° C.

8. The method according to claim 1 wherein extracting step (iv) is performed at a pH value in the range of pH 1-10.

9. The method according to claim 1 wherein extracting step (iv) is performed at a pH value in the range of pH 2-9.

10. The method according to claim 1 wherein extracting step (iv) is performed at a pH value in the range of pH 3-7.

11. A method of obtaining a product containing at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3-β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,12Z,15Z trienoyloxy)propanyl octadeca-9Z,12Z,15Z-trienoate, 3-α-D-glucopyranosyloxy-2-(octadeca-9Z,12Z,15Z-trienoyloxy) propanyl octadeca-9Z,12Z,15Z-trienoate, and mixtures said method consisting of the following steps, taken in sequence, of:

obtaining a plant material which contains at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3-β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,12Z,15Z trienoyloxy)propanyl octadeca-9Z,12Z,15Z-trienoate, 3-α-D-glucopyranosyloxy-2-(octadeca-9Z,12Z,15Z-trienoyloxy)propanyl octadeca-9Z,12Z,15Z-trienoate, and mixtures thereof;

(i) optionally milling the plant material, (ii) extracting the optionally milled plant material with water and producing a first liquid phase and a first solid phase which contains the at least one glycoside of a mono- or diacylglycerol;

(iii) separating the first liquid phase from the first solid phase, wherein the separated first liquid phase comprises a liquid product containing a glycoside of mono- or diacylglycerol, (iv) extracting the first solid phase obtained from step (iii) with water and producing a second liquid phase and a second solid phase which contains the at least one glycoside of a mono- or diacylglycerol, and, (v) separating the second liquid phase from the second solid phase to obtain in the second solid phase a solid concentrate product containing a concentrate of the at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3-β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,I2Z,I5Z trienoyloxy)propanyl octadeca-9Z,12Z,15Z-trienoate, 3-α-D-glucopyranosyloxy-2-(octadeca-9Z,12Z,15Z-trienoyloxy)propanyl octadeca-9Z,12Z,15Z-trienoate, wherein no organic solvents are used in any of steps i-v, and, drying the solid concentrate product.

12. The method according to claim 1 wherein the separated second liquid phase comprises a liquid product containing a glycoside of mono- or diacylglycerol.

13. A method of obtaining a product containing at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,I2Z,I5Z trienoyloxy)propanyl octadeca-9Z,12Z,15Z-trienoate, 3-α-D-glucopyranosyloxy-2-(octadeca-9Z,12Z,15Z-trienoyloxy) propanyl octadeca-9Z,12Z,15Z-trienoate, and mixtures thereof from a plant material, said method consisting essentially of the following steps, taken in sequence, of:

obtaining a plant material which contains at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3β-D-glucopyranosyloxy-2-(octadeca-9Z,12Z,15Z-trienoyloxy)propanyl octadeca-9Z,12Z,15Z-trienoate, 3-α-D-galactopyranosyloxy-2-(octadeca-9Z,I2Z,I5Z trienoyloxy)propanyl octadeca-9Z,12Z,15Z-trienoate, 3-α-D-glucopyranosyloxy-2-(octadeca-9Z,12Z,15Z-trienoyloxy)propanyl octadeca-9Z,12Z,15Z-trienoate, and mixtures thereof;

(i) optionally milling the plant material,
(ii) extracting the optionally milled plant material with water and producing a first liquid phase and a first solid phase which contains the at least one glycoside of a mono- or diacylglycerol;
(iii) separating the first liquid phase from the first solid phase,
(iv) extracting the first solid phase obtained from step (iii) with water and producing a second liquid phase and a second solid phase which contains the at least one glycoside of a mono- or diacylglycerol, and,
(v) separating the second liquid phase from the second solid phase to obtain in the second solid phase a solid concentrate product containing a concentrate of the at least one glycoside of a mono- or diacylglycerol selected from the group consisting of 3 β-D-galactopyranosyloxy-2-(octadeca-9Z,12Z,15Z-trienoyloxy)propanyl octadeca-9Z,12Z,15Z-trienoate, 3β-D-glucopyranosyloxy-2-(octadeca-9Z,12Z,15Z-trienoyloxy)propanyl octadeca-9Z,12Z,15Z-trienoate, 3-α-D-galactopyrano-syloxy-2-(octadeca-9Z,I2Z,I5Z trienoyloxy)propanyl octadeca-9Z,12Z,15Z-trienoate, 3-α-D-glucopyranosyloxy-2-(octadeca-9Z,12Z,15Z-trienoyloxy)propanyl octadeca-9Z,12Z,15Z-trienoate, and mixtures thereof, wherein no organic solvents are used in any of steps i-v; and, wherein the separated first liquid phase comprises a first product containing a glycoside of mono- or diacylglycerol, the separated second liquid phase comprises a second product containing a glycoside of mono- or diacylglycerol, and a third product is the separated second solid phase comprising the solid concentrate product containing the at least one glycoside of mono- or diacylglycerol.

14. The method according to claim 13 further comprising adding a cell wall degrading enzyme or a mixture of cell wall degrading enzymes to the water containing the optionally milled plant material in the extracting step (ii) to degrade cell walls of the plant material.

15. The method according to claim 14 wherein the cell wall degrading enzyme or mixture of cell wall degrading enzymes is one or more degrading enzymes selected from the group consisting of cellulase, β-glucanase, xylanase, arabanase and pentosanase.

16. The method according to claim 14 further comprising, before separating step (iii), inactivating the cell wall degrading enzyme or mixture of cell wall degrading enzymes by either heating the mixture of the water and the optionally milled plant material or by adding an acid or a base thereto.

17. The method according to claim 13 further comprising, during extraction step (iv), adding a cell wall degrading enzyme or a mixture of cell wall degrading enzymes to the water and the first solid phase to degrade cell walls of the plant material contained therein.

18. The method according to claim 17 further comprising, prior to step (v), inactivating the cell wall degrading enzyme or the mixture of cell wall degrading enzymes by either heating the water containing the first solid phase or by adding an acid or a base thereto.

19. The method according to claim 17 wherein the cell wall degrading enzyme or mixture of cell wall degrading enzymes is one or more degrading enzymes selected from the group consisting of cellulase, β-glucanase, xylanase, arabanase and pentosanase.

20. The method according to claim 13 further comprising drying the solid concentrate product.

21. The method according to claim 13 further comprising mixing the water in step (ii) or the water in step (iv) with the plant material or the first solid phase at a ratio of 50:1 to 1:50.

22. The method according to claim 13 further comprising mixing the water in step (ii) or the water in step (iv) with the plant material or the first solid phase at a ratio of 25:1 to 1:25.

23. The method according to claim 13 further comprising mixing the water in step (ii) or the water in step (iv) with the plant material or the first solid phase at a ratio of 10:1 to 1:10.

24. The method according to claim 13 further comprising performing the extracting step (iv) at an extraction temperature in the range of 20-75° C.

25. The method according to claim 13 further comprising performing the extracting step (iv) at an extraction temperature in the range of 30-60° C.

26. The method according to claim 13 further comprising performing the extracting step (iv) at an extraction temperature in the range of 40-55° C.

27. The method according to claim 13 further wherein extracting step (iv) is performed at a pH value in the range of pH 1-10.

28. The method according to claim 13 wherein extracting step (iv) is performed at a pH value in the range of pH 2-9.

29. The method according to claim 13 wherein extracting step (iv) is performed at a pH value in the range of pH 3-7.

* * * * *